United States Patent [19]

Langer et al.

[11] Patent Number: 4,478,805

[45] Date of Patent: Oct. 23, 1984

[54] PREPARATION OF HIGH PURITY BERLINITE

[75] Inventors: Horst G. Langer, Wayland, Mass.; Jere D. Fellmann, Livermore, Calif.

[73] Assignee: The Dow Chemical Company, Midland, Mich.

[21] Appl. No.: 534,906

[22] Filed: Sep. 22, 1983

[51] Int. Cl.³ .............................................. C01B 25/36
[52] U.S. Cl. .................................................... 423/311
[58] Field of Search ............................... 423/308, 311

[56] References Cited

U.S. PATENT DOCUMENTS 4,324,773 4/1982 Chal et al. ............................ 423/311

FOREIGN PATENT DOCUMENTS 634837 3/1950 United Kingdom ................ 423/311

OTHER PUBLICATIONS

CA50:12717d J. Papailhau, *Compt. Rend.*, 242, 1191 (1956).
CA78:58098c; M. Tsuhako, *Nippon Kagku Zasshi*, 92(4), 318–22 (1971).
CA74:27559d; A. G. Kotlova, *Izr. Akad. Nauk SSSR Neorg Mater*, 1970, 6(11), 2075.

Primary Examiner—John Doll
Assistant Examiner—Wayne A. Langel
Attorney, Agent, or Firm—Douglas N. Deline

[57] ABSTRACT

High purity berlinite is prepared by formation of an organoaluminum phosphate hydrogel in an organic solvent and subsequently hydrolyzing the hydrogel by reaction with water at pH less than or equal to 3.0. The berlinite is useful as a replacement for silicon-based quartz in electronic applications and in piezoelectric devices.

10 Claims, No Drawings

PREPARATION OF HIGH PURITY BERLINITE

BACKGROUND OF THE INVENTION

Berlinite is anhydrous aluminum phosphate in the quartz form. It may be prepared by heating precipitated, amorphous aluminum phosphate to high temperature (823° K) in the presence of lithium fluoride. J. Papailhau, *Compt. Rend.*, 242, 1191 (1956). Berlinite may also be prepared by direct reaction of alumina with phosphoric acid. M. Tsuhako et al., Nippon Kagku Zasshi, 92, 318 (1971). It is also known to employ aluminum trichloride in the reaction with phosphoric acid and sodium hydroxide (CA74:27559d).

Berlinite is of commercial value due to its piezoelectric and electronic properties. High quality berlinite may be suitably employed as an alternative to quartz in surface acoustic wave piezoelectric devices. For such applications it is imperative that the berlinite crystals be of extremely high purity. In particular, iron, sodium and silicon impurities are desirably substantially absent, and water content must be extremely low. Where relatively large nutrient crystals of berlinite are employed as seed crystals, the avoidance of water entrapment is highly important.

Previously known methods of preparing berlinite have not proven acceptable in order to prepare an extremely high purity product suitable for electronic applications. Accordingly, it would be desirable to provide a process for the preparation of high purity berlinite. It would further be desirable to provide a process that allows for the ready preparation of high purity berlinite at modest cost in both equipment employed and in energy consumed.

SUMMARY OF THE INVENTION

According to the present invention, there is provided an improved process for preparing high purity berlinite comprising:

(1) forming in an organic solvent an organoaluminum phosphate hydrogel having an aluminum to phosphorus atomic ratio of from about 1:1 to about 1:1.2 comprising at least one compound corresponding to the formula

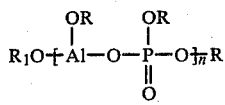

where each R is hydrogen or $R_1$, and $R_1$ is an alkyl, dialkylaminoalkyl or alkoxyalkyl group of up to about 10 carbons;

(2) hydrolyzing the organoaluminum phosphate hydrogel by heating in the presence of water at a pH of less than about 3.0 to thereby form berlinite; and (3) recovering the berlinite.

Preferably the berlinite prepared according to the present invention is of extremely high purity, having less than about 15 ppm of iron, less than about 30 ppm silicon and less than about 60 ppm sodium impurities and especially suited for use in electronic applications.

DETAILED DESCRIPTION OF THE INVENTION

The initial step in preparation of berlinite according to the present invention is in the preparation of a stable organoaluminophosphate hydrogel in an organic solvent having an aluminum to phosphorus ratio of from about 1:1 to about 1:1.2. Accordingly, such organoaluminophosphate hydrogel (hereinafter hydrogel) may be prepared by reacting an aluminum alkoxide or hydrogen aluminum alkoxide with phosphoric acid or phosphorus pentoxide in an organic solvent. The reaction is conducted in the substantial absence of water.

Suitable aluminum alkoxides or hydrogen aluminum alkoxides are those corresponding to the formula Al(OR$_1$)$_3$ or HAl(OR$_1$)$_4$ where $R_1$ is as previously defined. In particular, $R_1$ may be selected from methyl, ethyl, isopropyl, n-butyl, sec-butyl, tert-butyl, n-hexyl, methoxy ethyl, ethoxyethyl, butoxyethyl, dimethylaminoethyl, etc. Mixed aluminum alkoxides may also be employed. Preferably $R_1$ is butoxyethyl or sec-butyl.

Suitable organic solvents include aliphatic and aromatic hydrocarbons or halogenated derivatives thereof. Examples are methylene chloride, hexane, kerosene, toluene, ethylbenzene, diethylbenzene, etc. Preferred solvents are those having a normal boiling point above about 100° C. An especially preferred solvent is toluene.

The reaction is accomplished by contacting the two reactants optionally at elevated temperatures. The reaction may be conducted at reflux or at elevated, e.g., autogenous pressures. In the case of reaction with P$_2$O$_5$, the aluminum alkoxide is refluxed in the organic solution with a quantity of phosphorus pentoxide. Preferably, the phosphorus pentoxide is employed as a finely ground powder. In this manner, the P$_2$O$_5$ particles are not as likely to become unreactive due to the accumulation of a surface coating of gelatinous hydrogel reaction product.

A preferred phosphorus reactant is phosphoric acid which readily reacts with an organic solution of the aluminum alkoxide even at ambient temperature to provide a uniform hydrogel.

An alternative process for preparing the hydrogel is to react metallic aluminum with a partial ester of diphosphoric acid corresponding to the formula

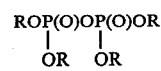

where R is as previously defined, provided, that in at least one occurrence R is hydrogen. The reaction is conducted in an inert organic solvent. After reaction, small amounts of an aluminum alkoxide may be added to the reaction mixture to adjust the atomic ratio of aluminum: phosphorus to the desired ratio of about 1:1 to 1:1.2.

Preparation of the above hydrogels has previously been described and patented by one of us and another in U.S. Pat. No. 4,301,025, which teaching is incorporated herein by reference.

Hydrolysis of the above hydrogel is accomplished at elevated temperatures. Suitable temperatures are from about 90° C. to about 200° C., and preferably from about 120° C. to about 160° C. Ambient pressures such as are present where a reflux condenser is employed or elevated pressures may suitably be employed.

During the hydrolysis under reflux conditions, it is preferred to employ a small excess of free phosphoric acid and also free alcohol, $R_1$OH. The presence of alcohol aids in the rate of formation of the desired berlinite crystals while the acid is necessary for conversion of the hydrogel to the desired crystal structure. Excess phosphoric acid, from about 0.1 to about 0.5 equivalents more than stoichiometric is preferably added to the refluxing solution. The amount of alcohol added is preferably from about 0.4 to about 1.0 mole per mole of phosphorus present in the hydrogel. Use of excess alcohol and phosphoric acid is not as important when employing elevated pressures but may be employed if desired.

To prepare berlinite having the best crystal size and purity under reflux conditions it is preferred to remove excess water from the reaction mixture. Suitably the water may be removed by azeotropic action.

Heating may be continued for several hours or even days until suitable amounts of berlinite are prepared. Additional forms of aluminum phosphate such as crystobalite and unchanged hydrogel as well as amorphous and other crystalline aluminum phosphates may be formed by the hydrolysis process. Generally, adjusting the reaction mixture by addition of small amounts of water, acid, alcohol and seed crystals of the desired berlinite may be employed to raise or lower the amount of berlinite formed, the crystalline size, the rate of crystal formation and other parameters of the reaction process.

Formation of berlinite is apparently obtained by the simultaneous hydrolysis and dehydration of the hydrogel. It is believed without wishing to be bound by such belief that the reaction mechanism involves the hydrolysis of the ester moieties of the organohydrogel by action of acid leading to the release of the alcohol $R_1OH$. The alcohol product aids in solubilizing further phosphoric acid due to partial esterification thereof. At the same time, the released alcohol aids in dehydration of the resulting product by the extraction of excess water from the reaction mass.

The berlinite formed by the process may be washed free of the intermediate phase impurities with water. After washing, the crystals of berlinite may simply be filtered free of the organic solvent and dried optionally with gentle heating. Due to the relative purity of the crystals they are extremely useful as seed crystals for further crystal propagation of berlinite from solutions of aluminum phosphate.

SPECIFIC EMBODIMENTS

Having described the present invention, the following examples are provided as further illustrative thereof and are not to be construed as limiting. In the examples, the butoxyethanol employed is dried over activated 4 angstrom molecular sieves and used without further purification. Either reagent grade or ultra high purity (UHP) phosphoric acid may be employed. High purity aluminum of purity 99.999999 percent is used to prepare the aluminum alkoxide.

Reflux reactions are carried out in 250-ml 3-neck flasks fitted with a nitrogen inlet and a mechanical stirrer. The UHP reactions are carried out similarly, however, the glassware is cleaned first with concentrated hydrogen chloride followed by rinsing with a solution of potassium hydroxide in ethanol and washing in water. The pressure reactions are performed in 50-ml Fischer-Porter bottles with a standard head coupler connected to a manifold containing a pressure gauge, exhaust valve, and a pressure release valve set to 100 psig.

Powder X-ray diffraction patterns are obtained on a Rigaku "Miniflex" diffractometer, equipped with a 1-KW, Cu target X-ray tube and sealed-off proportional counter. The patterns are recorded on strip chart between 100° and 3° at a rate of 2°/minute.

Differential scanning calorimetry and thermogravimetric analysis spectra are obtained on the DuPont 1090 Thermal Analyzer equipped with a 910 differential scanning calorimeter and a 951 thermogravimetric analyzer. Spectra are obtained in air from ambient temperature to 620° C. with a heating rate of 20° C./minute.

EXAMPLE 1

Preparation of Aluminum Alkoxide

Three 10-g aluminum ingots (1.11 moles) are placed in a soxhlet extractor. Dry 2-n-butoxyethanol (527.5 g, 4.44 moles) is placed into a 3-neck one-liter flask. Approximately 1 ml of previously prepared tetra-alkoxide, $HAl(OC_2H_4OC_4H_9)_4$, is dropped onto the ingots. The system is purged with $N_2$ for 16 hours. The 2-butoxyethanol is slowly heated with stirring to cause condensation onto the metal. After initiation of reaction, evidenced by pitting of the aluminum surface, heating is increased to cause a gentle reflux. After 6 hours of heating, all aluminum is consumed. The product, $HAl(OC_2H_4OC_4H_9)_4$, is transferred to polyethylene bottles for storage.

Preparation of Berlinite Under Hydrothermal Conditions $P_2O_5$ (28.5 g, 0.2 mole) is added to 200 ml of methylene chloride to form a slurry. The alkoxide, $HAl(OC_2H_4OC_4H_9)_4$ (50.5 g), is dissolved in 200 ml of methylene chloride and slowly added to the $P_2O_5$ slurry. An exothermic reaction results and all $P_2O_5$ dissolves, resulting in a viscous dark colored organo aluminum phosphate hydrogel having an empirical formula of $H(Al(OC_2H_4OC_4H_9)_4P)$.

The above hydrogel (52.7 g, 0.1 mole) and $HAl(OC_2H_4OC_4H_9)_4$ (49.6 g, 0.1 mole) are combined in methylene chloride (100 ml) and the resulting gel is stirred. Aqueous isobutanol, 50 percent by volume (100 ml) is added and the resulting solution heated. The gel dissolves, then a viscous oily material separates. Upon continued heating a fluffy precipitate results. Heating 2 g of the precipitate in 50 ml of water in a glass-lined pressure vessel to about 190° C. for 12 days at autogenous pressure transforms the precipitate into berlinite. The pH of the reaction solution is found to be about 2.0.

EXAMPLE 2

PREPARATION OF BERLINITE UNDER HYDROTHERMAL CONDITIONS

An organoaluminumphosphate hydrogel is prepared employing dimethylethanolamine. Accordingly, 23.9 g (0.886 mole) of aluminum is slowly added to dimethylethanolamine (237 g, 2.66 moles) at 100° C. Heating is continued until all aluminum is consumed and hydrogen evolution ceases. The alkoxide so formed, $Al(OC_2H_4N(CH_3)_2)_3$ (85.7 g, 0.294 mole), is placed in a flask under nitrogen containing 200 ml of toluene. Next, phosphorus pentoxide (20.5 g, 0.147 mole) is added. The resulting slurry is heated to 100° C. for 5 hours after which 5.3 ml of deionized water is added dropwise. The material is filtered, dried and ground to a powder. The resulting organoaluminumphosphate hydrogel has the empirical formula $Al(OC_2H_4N(CH_3)_2)_3 \cdot \frac{1}{2}P_2O_5$.

Phosphoric acid is added to 1000 ml of water until a pH of 1.9 is obtained. Sodium hydroxide solution (1.0 N) is added to bring the pH to 2.0. To 60 ml of the adjusted solution is added 1 g of the above gel mixture and the resulting mixture is vigorously stirred to break up clumps. An ammonium salt, tetraisopropoxyammonium bromide (1.5 g), is added. The pH is again adjusted to provide a pH of 2.0. The solution is placed in a glass-lined pressure reactor and heated to 160° C. for 6 days under autogenous pressure. The resulting crystals are isolated by filtration, washed with water and dried at 100° C. for 16 hours. The isolated product is identified as berlinite by X-ray powder diffraction.

EXAMPLE 3

PREPARATION OF BERLINITE UNDER REFLUX CONDITIONS

Toluene (65 ml) is added to $H(Al(OC_2H_4OC_4H_9)_4)$ (50 g, 0.1 mole) prepared substantially according to the procedure of Example 1. UHP phosphoric acid (14.3 g, 0.124 mole) is added dropwise to form an organoaluminum phosphate hydrogel. Next, 40 drops of deionized water are slowly added. The mixture is warmed and heated at reflux for 8 hours, then cooled and stirred an additional 8 hours and finally refluxed until all gel disappears and only crystalline product remains. Both needle-like crystals of an intermediate phase and smaller crystals identified as berlinite are present. Continued heating at reflux results in substantially pure berlinite. Analysis by emission spectroscopy indicates the berlinite contains about 13 ppm Fe, 29 ppm Si and less than 10 ppm Na.

EXAMPLE 4

In a glass pressure vessel, toluene (40 ml) and $HAl(OC_2H_4OC_4H_9)_4$ (16.4 g, 0.033 mole) are combined and mixed thoroughly. Phosphoric acid (85 percent) (0.033 mole) is then added and mixed thoroughly. The vessel is placed in an oil bath at 140° C. and stirred for 5 days. During the reaction, a pressure of about 20 psi is attained. The reactor is then cooled and water (100 ml) added. The resulting berlinite product is recovered by filtration, washed with water and oven dried at 100° C.

Analysis by emission spectroscopy indicates the product contains about 15 ppm Fe, less than 10 ppm Si and about 59 ppm Na.

What is claimed is:

1. A process for preparing berlinite comprising:
    (1) forming in an organic solvent an organoaluminum phosphate hydrogel having an aluminum to phosphorus atomic ratio of from about 1:1 to about 1:1.2 comprising at least one compound corresponding to the formula:

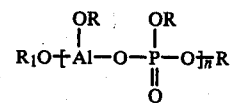

where each R is hydrogen or $R_1$, and $R_1$ is an alkyl, dialkylaminoalkyl or alkoxyalkyl group of up to about 10 carbons;
    (2) hydrolyzing the organoaluminum phosphate hydrogel by heating in the presence of water at a pH of less than about 3.0 to thereby form berlinite; and
    (3) recovering the berlinite.

2. A process according to claim 1 wherein the organic solvent is an aliphatic or aromatic hydrocarbon or halogenated derivative thereof.

3. A process according to claim 2 wherein the organic solvent has a boiling point above about 100° C.

4. A process according to claim 3 wherein the solvent is toluene.

5. A process according to claim 1 wherein $R_1$ is butoxyethyl or sec-butyl.

6. A process according to claim 1 wherein the organoaluminum phosphate hydrogel is formed by reacting an aluminum alkoxide or hydrogen aluminum alkoxide corresponding to the formula $Al(OR_1)_3$ or $HAl(OR_1)_4$ wherein $R_1$ is an alkyl, dialkylaminoalkyl, or alkoxyalkyl group of up to about 10 carbons, with phosphoric acid or phosphorus pentoxide.

7. A process according to claim 6 wherein the hydrolysis is performed by heating to at least about 90° C. up to about 200° C.

8. A process according to claim 7 wherein the temperature is about 160° C. and the hydrolysis is conducted in a sealed pressure reactor at elevated pressures.

9. A process according to claim 7 wherein the hydrolysis is obtained by refluxing at atmospheric pressure.

10. A process according to claim 9 wherein during the hydrolysis from about 0.1 to about 1 mole of alcohol of the formula $R_1OH$ per mole of hydrogel is added to the hydrolysis mixture prior to the hydrolysis reaction.

* * * * *